US009101142B1

(12) United States Patent
Chauhan et al.

(10) Patent No.: US 9,101,142 B1
(45) Date of Patent: Aug. 11, 2015

(54) METHODS AND COMPOSITIONS FOR REPELLING AND/OR KILLING INSECTS

(71) Applicant: The United States of America, as represented by the Secretary of Agriculture, Washington, DC (US)

(72) Inventors: Kamlesh R. Chauhan, Laurel, MD (US); Ulrich R. Bernier, Gainesville, FL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 14/444,150

(22) Filed: Jul. 28, 2014

Related U.S. Application Data

(62) Division of application No. 13/181,914, filed on Jul. 13, 2011, now Pat. No. 8,822,533.

(51) Int. Cl.

| | |
|---|---|
| ***A01N 53/00*** | (2006.01) |
| ***C07C 69/743*** | (2006.01) |
| ***C07C 13/04*** | (2006.01) |
| ***C07C 53/134*** | (2006.01) |

(52) U.S. Cl.
CPC .............. *A01N 53/00* (2013.01); *C07C 69/743* (2013.01); *C07C 13/04* (2013.01); *C07C 53/134* (2013.01)

(58) Field of Classification Search
CPC ...... A01N 53/00; C07C 69/743; C07C 13/04; C07C 53/134
USPC ........................................... 514/531; 560/124
See application file for complete search history.

(56) References Cited

U.S. PATENT DOCUMENTS

| | | | | |
|---|---|---|---|---|
| 4,405,640 | A * | 9/1983 | Punja | 514/531 |
| 6,225,495 | B1 * | 5/2001 | Ujihara et al. | 560/124 |
| 2005/0112163 | A1 * | 5/2005 | Nishimura et al. | 424/405 |

OTHER PUBLICATIONS

Elliott et. al., Pesticide Science, 1986, Society of Chemical Industry, vol. 17, No. 6, pp. 708-714.*

* cited by examiner

*Primary Examiner* — Sarah Pihonak
(74) *Attorney, Agent, or Firm* — John D. Fado; G. Byron Stover

(57) ABSTRACT

Unique volatile pyrethroids and a method for repelling and/or killing insects involving treating an object or area with an insect repelling effective amount or insect killing effective amount of at least one unique volatile pyrethroid and optionally a carrier. Also a method for repelling and/or killing insects involving treating an object or area with an insect repelling effective amount or insect killing effective amount of at least one compound selected from bioresmethrin, D-allethrin, ethofenprox, prallethrin, transfluthrin, permethrin, and mixtures thereof, and optionally a carrier; wherein the object or area is clothing or items attached to clothing.

3 Claims, No Drawings

METHODS AND COMPOSITIONS FOR REPELLING AND/OR KILLING INSECTS

This is a divisional of application Ser. No. 13/181,914 filed Jul. 13, 2011, which is herein incorporated by reference in its entirety.

BACKGROUND OF THE INVENTION

The present invention relates to unique volatile pyrethroids having the following formula:

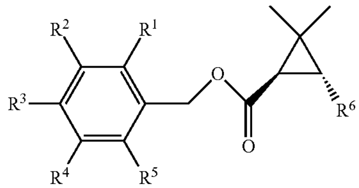

where $R^1$, $R^2$, $R^4$ and $R^5$ is H, Cl, F, O—$C_6H_6$, $OCH_3$, or $CH_2OCH_3$; $R^3$ is H, $CH_3$, $CH_2OCH_3$, Cl or F; and $R^6$ is HC═$C(CH_3)_2$, HC═$C(CF_3)$Cl, HC≡CH, HC═$CCl_2$, or HC═$CBr_2$. In addition, the unique volatile pyrethroids utilized herein may have the following formula:

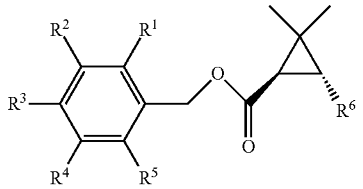

where $R^1$, $R^2$, $R^4$ and $R^5$ is F, H, O—$C_6H_6$; $R^3$ is H, and $R^6$ is HC═$C(CH_3)_2$, HC═$CCl_2$, or HC═$CBr_2$.

The present invention also relates to a method for repelling and/or killing insects involving treating an object or area with an insect repelling effective amount or insect killing effective amount of at least one unique volatile pyrethroid and optionally a carrier.

In addition, the present invention relates to a method for repelling and/or killing insects involving treating an object or area with an insect repelling effective amount or insect killing effective amount of at least one compound selected from bioresmethrin, D-allethrin, ethofenprox, prallethrin, transfluthrin, permethrin, and mixtures thereof, and optionally a carrier; wherein the object or area is clothing or items attached to clothing.

Diseases transmitted by blood-feeding insects are a serious threat to public health worldwide. More than 700 million cases of mosquito transmitted disease were reported annually (Shell, E. R., Atlantic Monthly, pp. 45-60, August 1997). Over three billion people live under the threat of malaria, which kills over a million people each year (WHO World Malaria Report 2005, Roll Back Malaria, World Health Organization, UNICEF, http://rbm.who.int/wmr2005). In the United States, West Nile virus was transmitted by mosquitoes to more than 8,000 people from 1999-2005, resulting in over 780 deaths (DeBiasi, R. L., and K. L. Tyler, Nat. Clin. Pract. Neurol., 2:264-275 (2006)). Ticks, mites and crawling insects like bedbugs are bloodsucking pests which are very difficult to control. Ticks are carrier of Lyme disease, causing outbreaks in many parts of north Americas, while bedbugs are the number one emerging threat to households, hotels, public places in metropolitan cities, and port of entries.

N,N-Diethyltoluamide (Deet) is considered to be the best insect repellent ever developed and is the most widely used insect repellent worldwide with tens of millions of dollars in annual sales (Osimitz, T. G., and R. H. Grothaus, J. Am. Mosq. Control. Assoc., 11: 274-278 (1995)). However, Deet dissolves plastics and paints, and clinical literature reports the association of Deet with neurotoxicity in humans (Robbins, P. J., and M. G. Cherniack, J. Toxicol. Environ. Health, 18: 503-525 (1986)). Thus, there is a great need for effective alternatives to Deet. Furthermore, all topical repellents, including Deet, require repeated applications for continued protection against biting insects. When using lower concentrations (<10%), topical repellents do not provide protection for nearby untreated surfaces, nor do they provide a spatial effect above treated surfaces to prevent mosquitoes from finding and biting hosts.

Pyrethroids are known to have significant insecticidal effects and are effective in repelling and/or killing blood sucking insects. Permethrin, a pyrethroid, was determined to be the best insect repellent for clothing and field treatment of U.S. military combat uniforms and has been used as the standard repellent treatment of uniforms since 1991. Since then uniform compositions have changed to incorporate nylon and, more recently, fire-resistant materials. Some uniforms now contain a wrinkle-free or permanent press finish. The change in fabric's composition, construction, weave, and finishes impact the retention and efficacy of permethrin used on uniforms. In almost all instances this impact has resulted in uniforms that afford less protection from insect bites.

Thus there is a need to increase the protection levels close to the ideal 100% protection from bites throughout the lifetime of the uniform. This requires either finding a faster acting alternative treatment to permethrin, or augmenting current permethrin-treatment of the uniform with faster acting volatile compounds to confer additional protection.

We have found new compounds which can be utilized, for example on clothing, to protect people from insect bites. We have also found that known compounds, previously never used on clothing, can also be utilized, for example on clothing, to protect people from insect bites.

SUMMARY OF THE INVENTION

In accordance with the present invention there is provided unique volatile pyrethroids having the following formula:

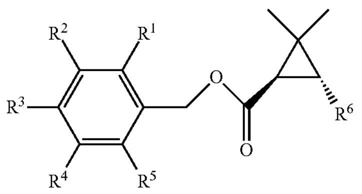

where $R^1$, $R^2$, $R^4$ and $R^5$ is H, Cl, F, O—$C_6H_6$, $OCH_3$, or $CH_2OCH_3$; $R^3$ is H, $CH_3$, $CH_2OCH_3$, Cl or F; and $R^6$ is HC═$C(CH_3)_2$, HC═$C(CF_3)$Cl, HC≡CH, HC═$CCl_2$, or HC═$CBr_2$. In addition, the unique volatile pyrethroids utilized herein may have the following formula:

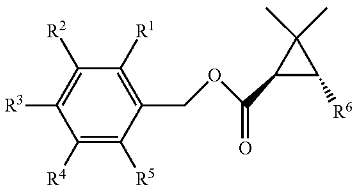

where $R^1$, $R^2$, $R^4$ and $R^5$ is F, H, O—$C_6H_6$; $R^3$ is H, and $R^6$ is HC═$C(CH_3)_2$, HC═$CCl_2$, or HC═$CBr_2$.

Also in accordance with the present invention there is provided a method for repelling and/or killing insects involving treating an object or area with an insect repelling effective amount or insect killing effective amount of at least one unique volatile pyrethroid and optionally a carrier.

Still in accordance with the present invention is a method for repelling and/or killing insects involving treating an object or area with an insect repelling effective amount or insect killing effective amount of at least one compound selected from bioresmethrin, D-allethrin, ethofenprox, prallethrin, transfluthrin, permethrin, and mixtures thereof, and optionally a carrier; wherein the object or area is clothing or items attached to clothing.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

DETAILED DESCRIPTION OF THE INVENTION

Disclosed herein are unique volatile pyrethroids and a method for repelling and/or killing insects involving treating an object or area with an insect repelling effective amount or insect killing effective amount of at least one unique volatile pyrethroid and optionally a carrier. Also a method for repelling and/or killing insects involving treating an object or area with an insect repelling effective amount or insect killing effective amount of at least one compound selected from bioresmethrin, D-allethrin, ethofenprox, prallethrin, transfluthrin, permethrin, and mixtures thereof, and optionally a carrier; wherein the object or area is clothing or items attached to clothing.

The invention concerns optimization of the deterrent/repellent effects of fast acting pyrethroids and application of optimized pyrethroids in a user friendly Velcro® system as well as barrier applications. The Velcro® system generally involves a strip of flexible cloth having a pocket into which is inserted a formulated pyrethroid pallet. This Velcro system can be attached over sleeves (cuffs), trousers, and collar of the shirt where biting insects like mosquitoes frequently attack. The insert pallet comprises formulation of the pyrethroids so that without blowing devices like fans, or heating of the formulation, active ingredients are dispersed thus forming a protective barrier.

We observed that volatile pyrethroids can be utilized for short durations (e.g., ranging from about 8 to about 10 hours) on Velcro® attachments to clothes. Attachments like Velcro® bands containing fast acting pyrethroids can enhance protection of treated uniforms up to 99% against disease vectors and blood sucking insects. We identified ligands responsible for spatial repellency, and modified pyrethroids with halogenated benzyl ester ligands, at the same time the cyclopropane moiety was substituted with novel acetylinic analogues to enhance repelling and/or insecticidal activities of pyrethroids. Evaluation of all pyrethroid analogs resembling this core ligand showed either equal or better mosquito repellency compared to transfluthrin. The Velcro® system is intended to be used as a stand-alone barrier or can be used with treated uniforms for bite proof protection against insect vectors.

We discovered that a core structure containing halogenated benzyl esters in pyrethroid analogs was a critical structural feature required for high vapor pressure. High vapor pressure is needed to form a barrier of protection due to volatilization of the compounds. Degree of halogenations as well as substitution pattern in the phenyl ring of pyrethroids facilitated various ranges of vapor pressure. We have used this information in designing range of vapor pressures among pyrethroids so that optimum vapor pressure is effectively used in the application of the compounds. In our in vitro bioassays all analogs based on this core structural feature showed promising deterrent/barrier effects compared to commercially available repellents or toxicants. In in vivo bioassays identical to those used to qualify companies to supply U.S. Marine Corps with factory-produced repellent-treated uniforms, the use of these pyrethroids analogs resulted in 100% bite protection. This level of protection was superior to the use of permethrin alone. Use of these halogenated pyrethroids analogs in strips affixed to the uniform by a Velcro® system is an ideal augmentation to improve significantly the protection of the uniform wearer from blood sucking insects such as mosquitoes and sand flies that vector disease and also from other insects of medical importance, such as ticks. None of the compounds described herein can be directly used on human skin.

The unique volatile pyrethroids utilized herein have the following formula:

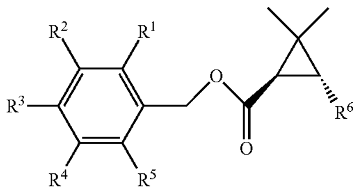

where $R^1$, $R^2$, $R^4$ and $R^5$ is H, Cl, F, O—$C_6H_6$, $OCH_3$, or $CH_2OCH_3$; $R^3$ is H, $CH_3$, $CH_2OCH_3$, Cl or F; and $R^6$ is HC═$C(CH_3)_2$, HC═$C(CF_3)Cl$, HC≡CH, HC═$CCl_2$, or HC═$CBr_2$. In addition, the unique volatile pyrethroids utilized herein may have the following formula:

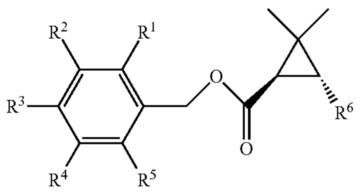

where $R^1$, $R^2$, $R^4$ and $R^5$ is F, H, O—$C_6H_6$; $R^3$ is H, and $R^6$ is HC═$C(CH_3)_2$, HC═$CCl_2$, or HC═$CBr_2$.

The following are specific examples of the unique volatile pyrethroids utilized below:

TL-I-141

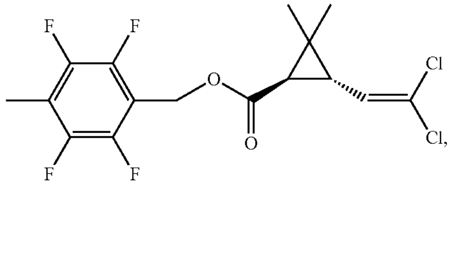

-continued

TL-I-107

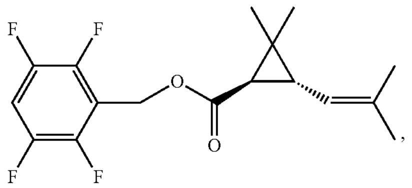

TL-I-105

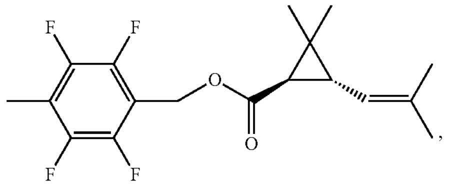

TL-I-73

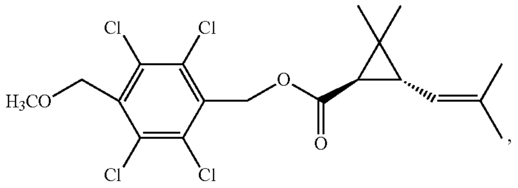

TL-I-111

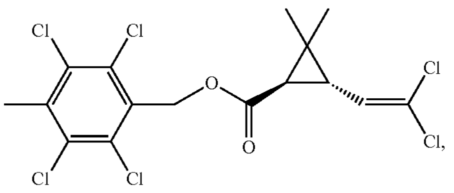

TL-I-113

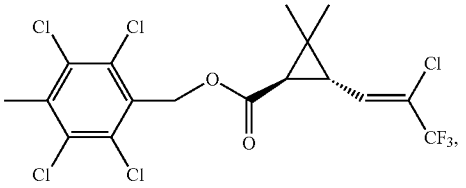

TL-III-23

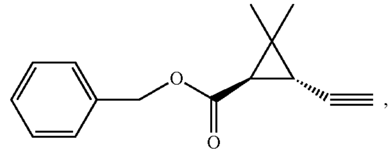

TL-III-25

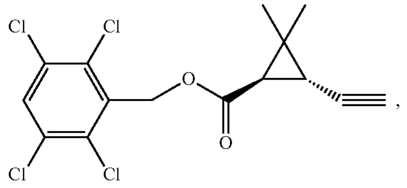

TL-III-27

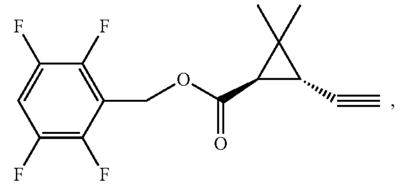

-continued

TL-III-29

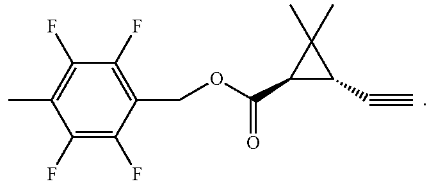

The following are examples of known pyrethroids which were never previously utilized as formulations on clothes, bed-nets, and pallets to be attached to clothes. These known volatile pyrethroids are now utilized in a novel application of spatial repellent and/or knockdown barrier formulated in pallet form to be attached on clothes using a Velcro system.

(TL-I-139)

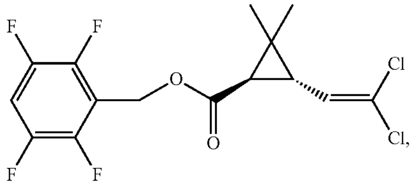

Transfluthrin

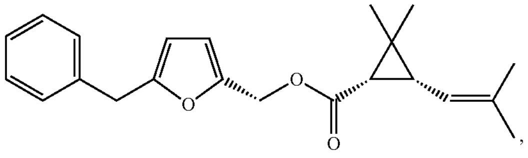

Bioresmethrin

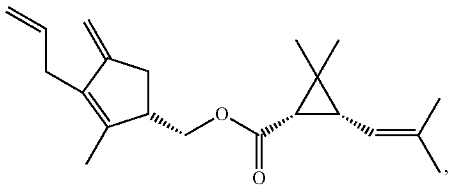

D-allethrin

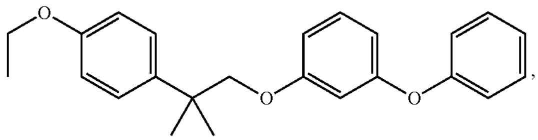

Ethofenprox

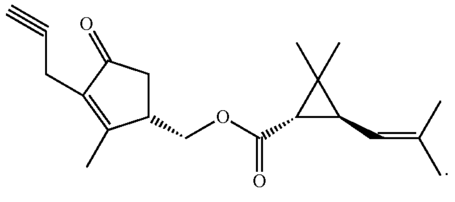

prallethrin

A method is disclosed for (1) repelling insects from an object (e.g., mammals such as humans) or area (e.g., a surface such as human skin or clothing) and/or for (2) killing insects, involving treating (or exposing) the object or area with a composition (1) containing a insect repelling effective amount of the compounds described herein or (2) containing an insect killing effective amount of the compounds described herein, and optionally a carrier material or carrier. The terms "object" or "area" as used herein include any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., luggage, bags, boxes, crates, etc.), packing materials, bedding, and so forth; also includes clothing.

An insect repellent is any compound or composition which deters insects from a host. Thus the term "repelling" is defined as causing insects (e.g., *Aedes aegypti, Anopheles albimanus, Phlebotomus papatasi*) to make oriented movements away from a source of a chemical repellent (Dethier, V. L., et al., J. Econ. Ent., 53: 134-136 (1960)) and also includes inhibiting feeding by insects when a chemical is present in a place where insects would, in the absence of the chemical, feed. Thus the term "repelling" also includes reducing the number of insect (e.g., *Aedes aegypti*) bites on a treated area or object (e.g., mammalian skin or clothing which has been treated topically with the compositions or compounds of the present invention) when compared to the same area or object which is untreated.

The amount of the compound used will be at least an effective amount. The term "effective amount," as used herein, means the minimum amount of the compound needed to cause insects to make oriented movements away from a treated area or object (e.g., clothing) which has been treated topically with the compound of the present invention) when compared to the same area or object which is untreated. The term "effective amount," as used herein, also means the minimum amount of the compound needed to reduce the number of insect (e.g., *Aedes aegypti*) bites on a treated area or object (e.g., mammalian skin or clothing which has been treated topically with the compound of the present invention) or the minimum amount of the compound needed to reduce the number of insect (e.g., *Aedes aegypti*) landings on a treated area or object (e.g., clothing which has been treated topically with the compound of the present invention) when compared to the same area or object which is untreated. Effective concentrations of the compound in the compositions may vary between about 0.1 and about 95% (e.g., 0.1-95%) by weight, preferably between about 0.5 and about 90% (e.g., 0.5-90%). Of course, the precise amount needed will vary in accordance with the particular repellent and/or insecticide composition used; the type of area or object to be treated; the number of hours or days of repelling and/or killing needed; and the environment in which the area or object is located. The precise amount of repellent and/or insecticide can easily be determined by one skilled in the art given the teaching of this application. For example, one skilled in the art could follow the procedures utilized below.

The compositions and compounds can therefore be used for repelling and/or killing harmful or troublesome blood-sucking and biting insects, ticks and mites. The term insects as used herein includes non-insects such as ticks and mites.

The blood-sucking insects include mosquitoes (for example *Aedes, Culex* and *Anopheles* species), sand flies (for example *Phlebotomus* and *Lutzomyia* species such as *Phlebotomus papatasi*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example *Melaphagus orinus*), fleas (for example *Pulex irritans, Cthenocephalides canis* and *Xenopsylla cheopis*) and sand fleas (for example *Dermatophilus penetrans*).

The biting insects include cockroaches (for example *Blattella germanica, Periplaneta americana, Blatta orientalis* and *Supella supellectilium*), beetles (for example *Sitophilus granarius, Tenebrio molitor, Dermestes lardarius, Stegobium paniceum, Anobium puntactum* and *Hylotrupes bajulus*), termites (for example *Reticulitermes lucifugus*) and ants (for example *Lasius niger*).

The ticks include, for example, *Ornithodorus moubata, Ixodes ricinus, Boophilus microplus* and *Amblyomma hebreum*, and mites include, for example, *Sarcoptes scabiei* and *Dermanyssus gallinae*.

Preferably, the blood-sucking and biting insects, ticks and mites include mosquitoes, sand flies, biting flies (e.g., black flies, biting midges), bed bugs, ticks, and fire ants (genus *Solenopsis*).

The compounds according to the invention, which can be used in undiluted or diluted form, can be converted into formulations customary for repellents and/or insecticides. They can be used in all the presentation forms customary in cosmetics, for example in the form of solutions, emulsions, gels, ointments, pastes, creams, powders, sticks, sprays or aerosols from spray cans. For use in the non-cosmetic sector, the compounds can be incorporated, for example, into granules, oily spraying agents or slow release formulations. The Velcro system was selected to provide insecticide treated fabric/wood chips/polymer strips which can be attached on any clothing, dress material, curtains, screens, etc. For example, the Velcro system could involve two pairs of Velcro strips carrying volatile pyrethroid formulation, one each on wrist area and one each on ankle, as well as one more on the collar for protection against biting insects. The formulation of pyrethroid and synergistic natural product is intended to use without any mechanical devise for effective release rate. For example, volatile pyrethroids like transfluthrin require mechanical devices or heat for dispersion into the atmosphere. However, by adding a volatile synergistic carrier like camphor or volatile essential oils it is possible to increase the vapor pressure of volatile pyrethroids, hence eliminating the need for mechanical devices like heat or battery operated fans.

The formulations are prepared in a known manner by mixing or diluting the compounds according to the invention with solvents (for example xylene, chlorobenzenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compounds according to the invention can be mixed with one another in the formulations or can also be used as mixtures with other known active compounds (for example sunscreen agents). The formulations in general contain between about 0.1 and about 95% (e.g., 0.1-95%) by weight of active compound, preferably between about 0.5 and about 90% (e.g., 0.5-90%).

For protection from insects such as blood-sucking insects or mites, the compounds according to the invention are generally either applied to human or animal skin, or items of clothing and other objects are treated with the compounds.

The compounds according to the invention are also suitable as an additive to impregnating agents for, for example, textile webs, articles of clothing and packaging materials, and as an additive to polishing, cleaning and window-cleaning agents.

The compositions of the present invention contain a carrier and the compound. The repellent and/or insecticide of the present invention is generally applied with a carrier component. The carrier component can be a liquid or a solid material. As is known in the art, the vehicle or carrier to be used refers to a substrate such as a gel, polymers, or the like. All of these substrates have been used to release insect repellents and/or insecticides and are well known in the art.

The compounds may be used with other repellents or insect control agents (e.g., insecticides, chemosterilants or the like). When used, these agents should be used in an amount which, as readily determined by one skilled in the arts, will not interfere with the effectiveness of the compound.

The compounds may be used with natural product (generally regarded as safe-GRAS) compounds, including but not limited to camphor, lemon eucalyptus oil, cedar oil, vetiver oil, etc. When used, these agents should be used in an amount which, as readily determined by one skilled in the arts, will not interfere with the effectiveness of the compound.

The compounds can also be used as toxicants and for preventing infestation of bedbugs. The compounds can also be as fumigants in hard to reach areas (e.g., luggage, clothes, furniture, bedding, etc.) through vapor action. The compounds are volatile insecticides which can permeate through porous spaces resulting in rapid mortality of insects without requiring direct application of the insecticides onto insects or onto the surfaces that insects contact.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Biological Evaluation: Bite protection assays were conducted with laboratory-reared 7-12 day old mosquitoes or sand flies. The species used throughout these studies are *Aedes aegypti* (Orlando, 1952) and *Phlebotomus papatasi* sand flies (Jerusalem, 1983). Females were pre-selected using either a hand draw box or a mechanical aspirator.

An assay was conducted by wearing sewn sleeves made from clothing material. Treated specimens were assayed with untreated controls to correct for the bite resistance afforded by material construction and composition. The untreated control was tested at the beginning of the experiment, followed by successively higher candidate repellent concentrations on sleeves. Sleeves were sewn from a cut out single ply trapezoidal pattern (33.2 cm×21 cm×25.5 cm height) of material. Sleeves were normally with a candidate repellent at the EPA permethrin label rate of 0.52% weight on (+5% tolerance) or less (0.125 mg/cm$^2$ for the 50/50 Nylon/Cotton (NYCO) Army Combat Uniform and 0108 mg./cm2 for the 65% Rayon/25% Para-aramid/10% Nylon Fire-Resistant Army Combat Uniform). Permethrin was 35:65cis:trans, 95.85% technical material. Experimental repellents were received as neat samples with <5% impurities. The treatment occurred by dissolution of repellent in suitable quantity of acetone to saturate the clothing, but minimizing excess solution. Excess solution was quantified and this amount of excess was then used to calculate the estimated amount of repellent applied to the material.

Insects were maintained in colony at approximately 78° F. and 60-80% RH. The photoperiod was 12:12. The mosquito cages were approximately 60000 cm$^3$ and each contained 175 to 225 female mosquitoes. The cages typically had a solid surface and either had 5 sides of mesh screen or had two plastic sides and 3 screened sides. Cages for sand fly work were slightly smaller (15000 cm$^3$) and constructed of acrylic for filming purposes and with screens on the exterior edges to allow air flow through the system. About 20-40 sand flies were released in cages for each assay. Assays started when the sleeved arm was inserted through the sleeve into the cage. Normally the hand was protected by a glove, but there were situations (i.e. sand fly data presented here) when the ability of a repellent to protect the untreated hand was determined. The assay periods were 15 min for the mosquitoes and 25-30 minutes for sand flies. The insects were allowed to land, probe and possibly bloodfeed during this time. At the conclusion of the experiment, all insects were knocked down or aspirated and the percentage that bloodfed of the total female test population in the cage was recorded. The protect level was calculated by Abbott's formula as a percentage reduction in bites compared to the untreated fabric control sleeve.

Specific conditions for bioassays are noted with corresponding data contained in the Tables.

As seen in Table 1, all experimental pyrethroids surprisingly provided 100% protection on ACU. In addition, the pyrethroid TL-I-139 (transfluthrin) was surprisingly superior to permethrin at protecting non-repellent treated surfaces of skin (i.e. the hand).

As seen in Table 2, all experimental pyrethroids surprisingly provided 100% protection on ACU. Treated specimens were stored in a cool dark location for one year and yet surprisingly retained their efficacy.

As shown in Table 3, FRACUs were more permeable and less absorptive due to the fabric composition and construction. This led to higher bite through (feeding) rates on permethrin-treated uniforms and, with permethrin, lower protection from bites compared to treatment of the Army Combat Uniform (ACU). Clearly the use of volatile pyrethroid, such as transfluthrin, surprisingly provided the ideal 100% protection from bites through fabric.

As shown in Table 4, surprisingly a semi-volatile pyrethroid or volatile pyrethroid treated strip significantly reduced biting through the untreated sleeve. The use of the more volatile pyrethroids, such as transfluthrin, surprisingly led to the ideal 100% bite protection on the FRACU, one of the more permeable U.S. Army uniforms.

As shown in Table 5, surprisingly a semi-volatile pyrethroid or volatile pyrethroid treated strip significantly reduced biting through the untreated sleeve. When the hand was unprotected, the use of permethrin on the uniform kept insects away from the uniform but led to increased bites on the skin in these kinds of bioassays. Incorporation of a volatile pyrethroid such as transfluthrin on a strip and affixed with Velcro® to a permethrin-treated uniform sleeve surprisingly led to significant protection from sand fly bites to the unprotected hand.

The data in Table 6 was acquired with the standard military repellent lotion applied to the exposed skin surface (the hand). This provided the most realistic estimate of performance from addition of a semi-volatile pyrethroid or volatile pyrethroid treated strip either with an untreated or permethrin-treated sleeve. The use of the more volatile pyrethroids surprisingly led to improved protective protection (83.2% to 100%) compared to a permethrin-treated uniform with repellent (71.5% protection) for the FRACU, one of the more permeable US Army uniforms.

We were able to examine several treatments on the FRACU fabric sleeves (Table 7). It was surprisingly demonstrated that a transfluthin sleeve at 0.52 mg/cm2 led to 100% bite protection of the Defender-M FRACU. Table 7 contains data for the examined candidates. The more volatile compounds surprisingly showed greater efficacy because of their ability to volatilize and affect the mosquito. The fastest acting compounds also surprisingly continued to be pyrethroids.

In vitro bioassays were conducted as described by Klun et. al. (Klun, J. A., et al., J. Med. Entomol., 40: 293-299 (2005)). Each test replicate consisted of 3 treatments: a control (EtOH); a standard (Deet, 4.54 nmol/μl); and an experimental compound (pyrethroid analogs, 4.54 nmol/ul). The 3 treatments were randomly assigned to consecutive cells in 2,6-cell reservoirs connected in series to a single water-bath pump; thus, 4 replicates could be tested/run. Tests were performed in an Air Science USA hood, with an air movement velocity of approx. 110-120 ft./min., temperature of 25-27° C., and RH of 15-25%. A 6-celled reservoir was connected to and heated by a constant-temperature (38° C.) water circulator (Lauda E100, Wobser GMGH and Co., Konigshofell, Germany).

Prior to each test, the upper surface of each reservoir was coated with a thin layer of high-vacuum silicone grease (Dow Corning Corp., Midland, Mich.), and the cells then filled (approx. 6 ml. capacity) or topped-off with either: (1) expired human red blood cells suspended in citrate-phosphate-dextrose-adenine (CPDA) solution, not more than 1 month past expiration date, and to which 110 mg ATP/35 ml. blood-CPDA had been added on the day of testing; or (2) CPDA+ATP $x^{-3}$, usually made up or diluted to $10^{-3}$ ATP on the day of testing. The filled cells were then covered with an Edicol collagen membrane (Devro, Sandy Run, S.C.) strip, and then with a just-treated (110 μl of 4.54 nmol/μl treatment or control solution) organdy cloth (G Street Fabrics, Rockville, Md.) strip. Mosquitoes used in tests were either *Aedes aegypti*_ (Liverpool) or *Anopheles stephensi*_Liston. K&D modules containing 5 adult females/cell were placed over a Teflon separator atop each reservoir; the sliding floors opened allowing access to the treated organdy cloth and membrane-covered cell; and the number of mosquitoes biting (proboscis inserted through the cloth) and/or observed to be engorged within each cell at the end of a 3-5 min. exposure period was recorded. Mosquitoes were used only once in a test, and then frozen and discarded.

Only tests in which 3 or more females fed in the control cell were analyzed, as lower feeding rates are indicative of substandard feeding readiness of that group of mosquitoes.

The knockdown and mortality of mosquitoes by exposure to candidate pyrethroids was evaluated by retaining exposed mosquitoes in the K&D chambers for 24 hrs once they were removed from the chemical exposure after 3 minutes of the base module. Data were collected to record knockdown in 6 minutes, one hour and 24 hours post exposure.

As shown in Table 8, TL-I-105, 107, 139 and 141 surprisingly exhibited 100% mortality up to 48 hours at 25 nM/cm2. At 2.5 nM/cm2 TL-I-105, 107, 139 and 141 surprisingly exhibited 100% mortality up to 24 hours, at 48 hrs there was 8-10% reduction in mortality.

Knockdown data and mortality for volatile pyrethroids against bed bugs (*Cimex lectularius*): Compounds were dissolved in acetone to yield concentrations of 100 μg/$cm^2$, 10 μg/$cm^2$, and 1 μg/$cm^2$ and 47 mm filter paper disks were treated. Acetone-treated filter paper was used as a negative control. Mixed stages (nymphs and adults) of a laboratory colony of the bed bug *Cimex lectularius* were placed on the treated filter paper in glass Petri dishes and mortality was recorded 24 h later, at which time bed bugs were removed to untreated surfaces. 24 h after this transfer another assessment of mortality was made to see if any dead or moribund bugs had recovered.

Compounds which surprisingly exhibited 100% mortality at 100 μg/$cm^2$, 10 μg/$cm^2$, and 5 μg/$cm^2$ (mortality at 1 μg/$cm^2$ shown in parentheses): TL-177 (20% at 1 μg/$cm^2$), I-105 (10%), I-107 (0%), I-109 (0%), I-111 (0%), I-113 (20%). Compounds that surprisingly exhibited no mortality or mortality less than 100% at either 100 μg/$cm^2$ or 10 μg/$cm^2$: TL-199, III-99, III-101, I-201, I-97, TL-I-139 transfluthrin (20%), acetone control 0% mortality. No recovery was observed at 24 h after removal to untreated filter paper.

Novel volatile pyrethroids, when evaluated against hard to reach creeping insects like bedbugs, showed excellent toxicity in vapor phase at microgram scale. This fact can be utilized for the development of formulations containing volatile pyrethroids in controlling infestations by bedbugs.

Table 9 shows halogenated pyrethroid analogues (all novel except TL-I-139).

All of the references cited herein, including U.S. Patents, are incorporated by reference in their entirety.

Thus, in view of the above, the present invention concerns (in part) the following:

A composition, comprising (or consisting essentially of or consisting of) at least one compound selected from the group consisting of compounds having the formula

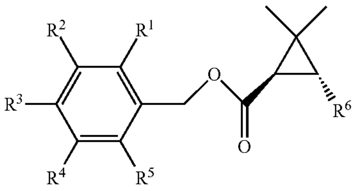

where $R^1$, $R^2$, $R^4$ and $R^5$ is H, Cl, F, O—$C_6H_6$, $OCH_3$, or $CH_2OCH_3$;

$R^3$ is H, $CH_3$, $CH_2OCH_3$, Cl or F; and $R^6$ is HC═C$(CH_3)_2$, HC═C$(CF_3)$Cl, HC≡CH, HC═$CCl_2$, or HC═$CBr_2$; or where $R^1$, $R^2$, $R^4$ and $R^5$ is F, H, O—$C_6H_6$; $R^3$ is H, and $R^6$ is HC═C$(CH_3)_2$, HC═$CCl_2$, or HC═$CBr_2$; and optionally a carrier.

The above composition, wherein $R^1$, $R^2$, $R^4$ and $R^5$ is H, Cl, F, O—$C_6H_6$, $OCH_3$, or $CH_2OCH_3$; $R^3$ is H, $CH_3$, $CH_2OCH_3$, Cl or F; and $R^6$ is HC═C$(CH_3)_2$, HC═C$(CF_3)$Cl, HC≡CH, HC═$CCl_2$, or HC═$CBr_2$.

The above composition, wherein $R^1$, $R^2$, $R^4$ and $R^5$ is F, H, O—$C_6H_6$; $R^3$ is H, and $R^6$ is HC═C$(CH_3)_2$, HC═$CCl_2$, or HC═$CBr_2$.

The above composition, wherein said at least one compound is selected from the group consisting of

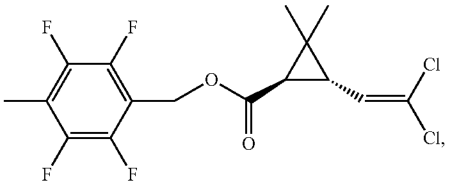

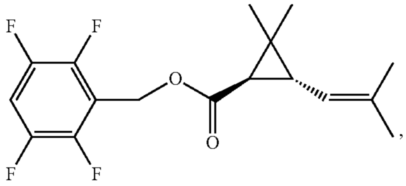

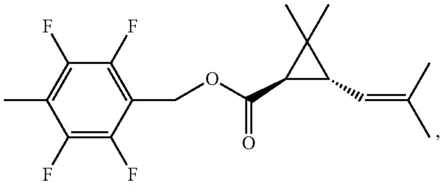

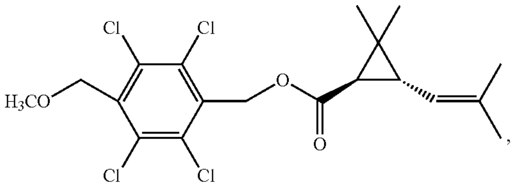

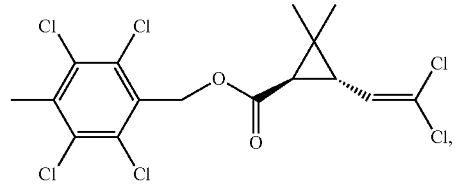

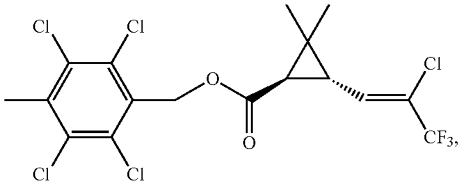

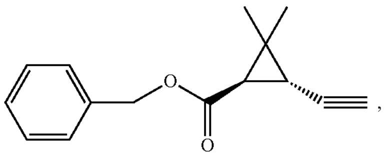

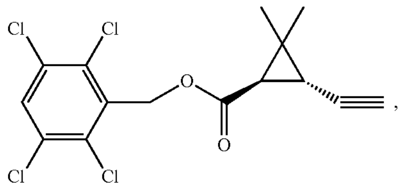

-continued

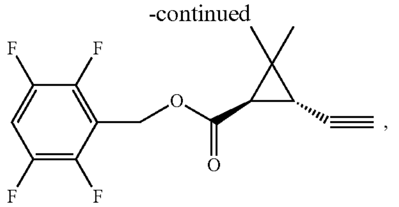

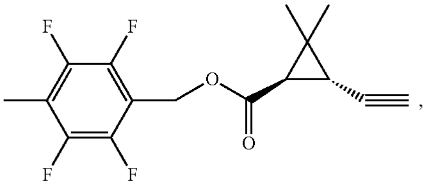

and mixtures thereof.

The above composition, wherein $R^1$, $R^2$, $R^4$ and $R^5$ is Cl or F; $R^3$ is H, $CH_3$, $CH_2OCH_3$ and $R^6$ is $HC{=}C(CH_3)_2$, $HC{=}C(CF_3)Cl$, $HC{\equiv}CH$, $HC{=}CCl_2$, or $HC{=}CBr_2$.

The above composition, wherein said carrier is a volatile carrier. The above composition, wherein said carrier is camphor or a volatile essential oil.

A method for repelling and/or killing insects, said method comprising (or consisting essentially of or consisting of) treating an object or area with an insect repelling effective amount or insect killing effective amount of at least one compound selected from the group consisting of compounds having the formula

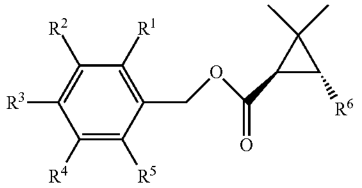

where $R^1$, $R^2$, $R^4$ and $R^5$ is H, Cl, F, $O{-}C_6H_6$, $OCH_3$, or $CH_2OCH_3$;

$R^3$ is H, $CH_3$, $CH_2OCH_3$, Cl or F; and $R^6$ is $HC{=}C(CH_3)_2$, $HC{=}C(CF_3)Cl$, $HC{\equiv}CH$, $HC{=}CCl_2$, or $HC{=}CBr_2$; or where $R^1$, $R^2$, $R^4$ and $R^5$ is F, H, $O{-}C_6H_6$; $R^3$ is H, and $R^6$ is $HC{=}C(CH_3)_2$, $HC{=}CCl_2$, or $HC{=}CBr_2$; and optionally a carrier.

A method for repelling and/or killing insects, said method comprising (or consisting essentially of or consisting of) treating an object or area with an insect repelling effective amount or insect killing effective amount of at least one compound selected from the group consisting of bioresmethrin, D-allethrin, ethofenprox, prallethrin, transfluthrin, permethrin, and mixtures thereof, and optionally a carrier; wherein said object or area is clothing or items attached to clothing.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Evaluation of permethrin and novel pyrethroids on the U.S. Army Combat Uniform (ACU) (50/50 NYCO) evaluated with *Ae. aegypti* mosquitoes. Last two tests are with glove removed from hand.

| Treatment (at concentration) + glove or no glove on hand | Bloodfed (#) | Total Population In Cage | Fed (%) | Bite Protection (%) |
|---|---|---|---|---|
| Control | 22 | 179 | 12.2 | — |
| Permethrin at 0.118 mg/$cm^2$ | 0 | 172 | 0.0 | 100 |
| Transfluthrin at 0.108 mg/$cm^2$ | 0 | 193 | 0.0 | 100 |
| TL-I-107 at 0.107 mg/$cm^2$ | 0 | 178 | 0.0 | 100 |
| TL-I-141 at 0.109 mg/$cm^2$ | 0 | 190 | 0.0 | 100 |
| TL-I-105 at 0.107 mg/$cm^2$ | 0 | 209 | 0.0 | 100 |
| TL-I-73 at 0.102 mg/$cm^2$ | 0 | 183 | 0.0 | 100 |
| Permethrin at 0.118 mg/$cm^2$ (No Glove) | 32 | 177 | 18.1 | — |
| Transfluthrin at 0.108 mg/$cm^2$ (No Glove) | 4 | 193 | 2.1 | — |

TABLE 2

Evaluation of permethrin and novel pyrethroids on the U.S. Army Combat Uniform (ACU) (50/50 NYCO) evaluated with *Ae. aegypti* mosquitoes. Treated specimens were stored in a laboratory refrigerator for one year and then tested.

| Treatment (at concentration) | Bloodfed (#) | Total Population In Cage | Fed (%) | Bite Protection (%) |
|---|---|---|---|---|
| Control | 38 | 180 | 21.1 | — |
| Permethrin at 0.118 mg/$cm^2$ | 0 | 199 | 0.0 | 100 |

TABLE 2-continued

Evaluation of permethrin and novel pyrethroids on the U.S. Army Combat Uniform (ACU) (50/50 NYCO) evaluated with *Ae. aegypti* mosquitoes. Treated specimens were stored in a laboratory refrigerator for one year and then tested.

| Treatment (at concentration) | Bloodfed (#) | Total Population In Cage | Fed (%) | Bite Protection (%) |
|---|---|---|---|---|
| Transfluthrin at 0.108 mg/$cm^2$ | 0 | 228 | 0.0 | 100 |
| TL-I-107 at 0.107 mg/$cm^2$ | 0 | 182 | 0.0 | 100 |
| TL-I-141 at 0.109 mg/$cm^2$ | 0 | 194 | 0.0 | 100 |
| TL-I-105 at 0.107 mg/$cm^2$ | 0 | 233 | 0.0 | 100 |
| TL-I-73 at 0.102 mg/$cm^2$ | 0 | 210 | 0.0 | 100 |

TABLE 3

Evaluation of permethrin and transfluthrin on the U.S. Army Fire Resistant Army Combat Uniform (FRACU) (65% Rayon, 10% Nylon, 25% Para-aramid) evaluated with *Ae. aegypti* mosquitoes.

| Treatment (at concentration) | Blood-fed (#) | Total Population In Cage | Fed (%) | Bite Protection (%) |
|---|---|---|---|---|
| Control | 145 | 185 | 78.4 | — |
| Permethrin at 0.071 mg/$cm^2$ | 24 | 237 | 10.5 | 86.7 |
| Combination: Permethrin at 0.031 mg/$cm^2$ + Transfluthrin at 0.038 mg/$cm^2$ | 0 | 230 | 0.0 | 100.0 |
| Transfluthrin at 0.052 mg/$cm^2$ | 0 | 213 | 0.0 | 100.0 |

TABLE 4

Evaluation of untreated and permethrin treated sleeves with a (20.5 cm × 2.6 cm) untreated, TL-I-73, or transfluthrin-treated fabric strips affixed with Velcro ® to the wrist region. Material was the U.S. Army Fire Resistant Army Combat Uniform (FRACU) (65% Rayon, 10% Nylon, 25% Para-aramid) and the test insects were *Ae. aegypti* mosquitoes. Hand was gloved for these experiments.

| Sleeve (Treatment and Concentration) | Strip (Treatment and Concentration) | Bloodfed (#) | Total Population In Cage | Fed (%) | Bite Protection (%) |
|---|---|---|---|---|---|
| Untreated (Control) | Untreated | 176 | 215 | 81.2 | — |
| Untreated | TL-I-73 at 0.163 mg/$cm^2$ | 71 | 203 | 10.5 | 57.2 |
| Permethrin 0.135 mg/$cm^2$ | Untreated | 10 | 204 | 4.9 | 94.0 |
| Permethrin 0.134 mg/$cm^2$ | TL-I-73 at 0.167 mg/$cm^2$ | 22 | 225 | 9.8 | 88.1 |
| Untreated | 0.158 mg/$cm^2$ Transfluthrin | 11 | 199 | 5.5 | 93.3 |
| Permethrin 0.134 mg/$cm^2$ | 0.161 mg/$cm^2$ Transfluthrin | 0 | 210 | 0.0 | 100.0 |

TABLE 5

Evaluation of untreated and permethrin treated sleeves with a (20.5 cm × 2.6 cm) untreated, TL-I-73, or transfluthrin-treated fabric strips affixed with Velcro ® to the wrist region. Material was the U.S. Army Fire Resistant Army Combat Uniform (FRACU) (65% Rayon, 10% Nylon, 25% Para-aramid) and the test insects were *Phlebotomus papatasi* sand flies. Hand was ungloved for these experiments. Assays were 25-29 minutes.

| Sleeve (Treatment and Concentration) | Strip (Treatment and Concentration) | Bloodfed (#) | Total Population In Cage | Fed (%) | Bite Protection (%) |
|---|---|---|---|---|---|
| Untreated (Control) | Untreated | 11 | 27 | 40.7 | — |
| Untreated | TL-I-73 at 0.163 mg/$cm^2$ | 7 | 22 | 31.8 | 21.8 |

TABLE 5-continued

Evaluation of untreated and permethrin treated sleeves with a (20.5 cm × 2.6 cm) untreated, TL-I-73, or transfluthrin-treated fabric strips affixed with Velcro ® to the wrist region. Material was the U.S. Army Fire Resistant Army Combat Uniform (FRACU) (65% Rayon, 10% Nylon, 25% Para-aramid) and the test insects were *Phlebotomus papatasi* sand flies. Hand was ungloved for these experiments. Assays were 25-29 minutes.

| Sleeve (Treatment and Concentration) | Strip (Treatment and Concentration) | Bloodfed (#) | Total Population In Cage | Fed (%) | Bite Protection (%) |
|---|---|---|---|---|---|
| Permethrin 0.135 mg/cm$^2$ | Untreated | 11 | 21 | 52.3 | −28.5 |
| Permethrin 0.134 mg/cm$^2$ | TL-I-73 at 0.167 mg/cm$^2$ | 10 | 21 | 47.6 | −16.9 |
| Permethrin 0.134 mg/cm$^2$ | 0.161 mg/cm$^2$ Transfluthrin | 1 | 41 | 2.4 | 94.1 |

TABLE 6

Evaluation of untreated and permethrin treated sleeves with a (20.5 cm × 2.6 cm) untreated, several volatile pyrethroids treated, or transfluthrin-treated fabric strips affixed with velcro to the wrist region. Material was the U.S. Army Fire Resistant Army Combat Uniform (FRACU) (65% Rayon, 10% Nylon, 25% Para-aramid) and the test insects were *Ae. aegypti* mosquitoes. Ultrathon 12 hr repellent (34.34% DEET) was applied to the hand.

| Sleeve (Treatment and Concentration) | Strip (Treatment and Concentration) | Bloodfed (#) | Total Population In Cage | Fed (%) | Bite Protection (%) |
|---|---|---|---|---|---|
| Untreated (Control) | Untreated | 50 | 187 | 26.7 | — |
| Untreated | TL-I-73 at 0.163 mg/cm$^2$ | 85 | 222 | 38.8 | −45% |
| Permethrin 0.135 mg/cm$^2$ | Untreated | 15 | 197 | 7.6 | 71.5 |
| Permethrin 0.134 mg/cm$^2$ | TL-I-73 at 0.163 mg/cm$^2$ | 3 | 203 | 1.5 | 94.5 |
| Untreated | 0.158 mg/cm$^2$ Transfluthrin | 6 | 205 | 2.9 | 89.2 |
| Permethrin 0.134 mg/cm$^2$ | 0.158 mg/cm$^2$ Transfluthrin | 0 | 202 | 0.0 | 100.0 |
| Permethrin 0.134 mg/cm$^2$ | 0.172 mg/cm$^2$ TL-III-23 | 1 | 200 | 0.5 | 98.1 |
| Permethrin 0.134 mg/cm$^2$ | <0.090 mg/cm$^2$ TL-III-25 | 7 | 188 | 3.7 | 86.1 |
| Permethrin 0.134 mg/cm$^2$ | 0.187 mg/cm$^2$ TL-III-27 | 1 | 206 | 0.5 | 98.2 |
| Permethrin 0.134 mg/cm$^2$ | 0.211 mg/cm$^2$ TL-III-29 | 9 | 200 | 4.5 | 83.2 |

TABLE 7

FRACUs (Defender-M) Treated with Insecticides.

| Specimen Type-Treatment | Conc (mg/cm$^2$) | Date (I) (m/d/y) | Date (F) (m/d/y) | Bite Protection (% ± SE) (*Ae. aegypti* + *An. albimanus*) |
|---|---|---|---|---|
| Allethrin | 0.085 | 10/26/10 | 10/29/10 | 98.7 ± 00.8 |
| Bioresmethrin | 0.106 | 10/06/10 | 10/22/10 | 98.1 ± 00.8 |
| Etofenprox | 0.101 | 10/06/10 | 10/22/10 | 94.9 ± 00.6 |
| Bifenthrin | 0.101 | 08/12/10 | 09/22/10 | 91.5 ± 01.1 |

TABLE 8

Biting protection and knockdown data for volatile pyrethroids in K&D module for pre-screening.

| Treatment | Concentration nM\cm$^2$ | Not feeding 3 minutes (%) | Knock-down 6 min (%) | Knock-down 1 hour (%) | Knockdown 24 hours (%) |
|---|---|---|---|---|---|
| Acetone | | 24 | 3 | 7 | 7 |
| a-cyper- | 2.5 | 81 | 67 | 91 | 100 |
| methrin | 25 | 98 | 83 | 100 | 100 |
| TL-73 | 2.5 | 100 | 97 | 100 | 100 |

TABLE 8-continued

Biting protection and knockdown data for volatile pyrethroids in K&D module for pre-screening.

| Treatment | Concentration nM\cm$^2$ | Not feeding 3 minutes (%) | Knock-down 6 min (%) | Knock-down 1 hour (%) | Knockdown 24 hours (%) |
|---|---|---|---|---|---|
| | 25 | 100 | 97 | 100 | 100 |
| TL-105 | 2.5 | 100 | 98 | 100 | 100 |
| | 25 | 100 | 100 | 100 | 100 |
| TL-107 | 2.5 | 100 | 100 | 100 | 100 |
| | 25 | 100 | 100 | 100 | 100 |
| TL-109 | 2.5 | 98 | 4 | 35 | 6 |
| | 25 | 98 | 4 | 58 | 37 |
| TL-111 | 2.5 | 90 | 0 | 16 | 8 |
| | 25 | 92 | 2 | 23 | 16 |
| TL-113 | 2.5 | 76 | 0 | 14 | 9 |
| | 25 | 92 | 0 | 34 | 23 |
| TL-117 | 2.5 | 57 | 0 | 0 | 2 |
| | 25 | 78 | 0 | 0 | 3 |
| TL-129 | 2.5 | 96 | 61 | 90 | 67 |
| | 25 | 99 | 100 | 100 | 100 |
| TL-131 | 2.5 | 98 | 11 | 29 | 15 |
| | 25 | 100 | 100 | 100 | 100 |
| TL-139 | 2.5 | 100 | 100 | 100 | 100 |
| | 25 | 100 | 100 | 100 | 100 |

TABLE 8-continued

| Biting protection and knockdown data for volatile pyrethroids in K&D module for pre-screening. | | | | | |
|---|---|---|---|---|---|
| Treatment | Concentration nM\cm$^2$ | Not feeding 3 minutes (%) | Knock-down 6 min (%) | Knock-down 1 hour (%) | Knockdown 24 hours (%) |
| TL-141 | 2.5 | 100 | 100 | 100 | 100 |
| | 25 | 100 | 100 | 100 | 100 |
| Trans-fluthrin | 2.5 | 100 | 100 | 100 | 100 |
| | 25 | 100 | 100 | 100 | 100 |

TABLE 9

Halogenated pyrethroid analogues (all novel except TL-I-139)

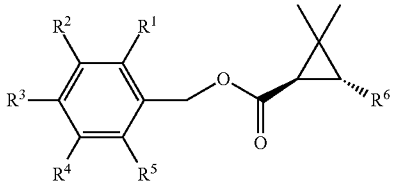

| | Name | $R^1$ | $R^2$ | $R^3$ | $R^4$ | $R^5$ | $R^6$ |
|---|---|---|---|---|---|---|---|
| 1. | TL-I-73 | Cl | Cl | $CH_2OCH_3$ | Cl | Cl | —(CH═C—$(CH_3)_2$) |
| 2. | TL-I-105 | F | F | $CH_3$ | F | F | —(CH═C—$(CH_3)_2$) |
| 3. | TL-I-107 | F | F | H | F | F | —(CH═C—$(CH_3)_2$) |
| 4. | TL-I-109 | Cl | Cl | $CH_3$ | Cl | Cl | —(CH═C—$(CH_3)_2$) |
| 5. | TL-I-111 | Cl | Cl | $CH_3$ | Cl | Cl | —(CH═C—$Cl_2$) |
| 6. | TL-I-113 | Cl | Cl | $CH_3$ | Cl | Cl | —(CH═C—Cl($CF_3$)) |
| 7. | TL-I-139 | F | F | H | F | F | —(CH═C—$Cl_2$) |
| 8. | TL-I-141 | F | F | $CH_3$ | F | F | —(CH═C—$Cl_2$) |
| 9. | TL-I-177 | F | F | $CH_3$ | F | F | —(CH═C—$Br_2$) |
| 10. | TL-III-23 | H | H | H | H | H | —(C≡CH) |
| 11. | TL-III-25 | Cl | Cl | H | Cl | Cl | —(C≡CH) |
| 12. | TL-III-27 | F | F | H | F | F | —(C≡CH) |
| 13. | TL-III-29 | F | F | $CH_3$ | F | F | —(C≡CH) |
| 14. | TL-I-91 | Cl | Cl | $CH_2OCH_3$ | Cl | Cl | —(CH═C—$Cl_2$) |
| 15. | TL-I-161 | F | F | CH3 | F | F | —(CH═C—Cl($CF_3$)) |
| 16. | TL-I-175 | F | F | H | F | F | —(CH═C—$Br_2$) |
| 17. | TL-III-79 | H | H | $CH_2OCH_3$ | F | F | —(C≡CH) |
| 18. | TL-III-81 | H | $OCH_3$ | H | H | H | —(C≡CH) |
| 19. | TL-III-83 | H | Ph | H | H | H | —(C≡CH) |

TABLE 9-continued

Halogenated pyrethroid analogues (all novel except TL-I-139)

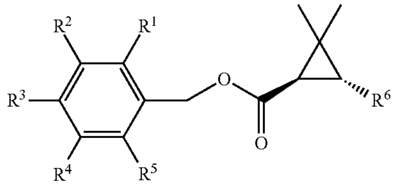

| | Name | $R^1$ | $R^2$ | $R^3$ | $R^4$ | $R^5$ | $R^6$ |
|---|---|---|---|---|---|---|---|
| 20. | KT-III-9 | F | F | F | F | H | —(CH═C—$Cl_2$) |
| 21. | KT-III-15 | F | F | F | F | H | —(CH═C—$(CH_3)_2$) |
| 22. | KT-III-49 | F | H | H | H | H | —(CH═C—$Cl_2$) |
| 23. | KT-III-51 | F | H | H | H | F | —(CH═C—$Cl_2$) |

The invention claimed is:

1. A composition, comprising at least one compound selected from the group consisting of compounds having the formula

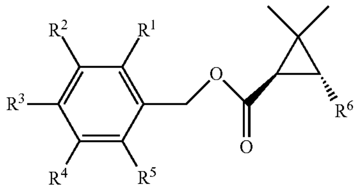

wherein where $R^1$ is H, $R^2$ is H, $R^3$ is H, $R^4$ is H, $R^5$ is H, and $R^6$ is HC≡CH;

wherein where $R^1$ is Cl, $R^2$ is Cl, $R^3$ is H, $R^4$ is Cl, $R^5$ is Cl, and $R^6$ is HC≡CH;

wherein where $R^1$ is F, $R^2$ is F, $R^3$ is H, $R^4$ is F, $R^5$ is F, and $R^6$ is HC≡CH;

wherein where $R^1$ is F, $R^2$ is F, $R^3$ is $CH_3$, $R^4$ is F, $R^5$ is F, and $R^6$ is HC≡CH;

wherein where $R^1$ is H, $R^2$ is H, $R^3$ is $CH_2OCH_3$, $R^4$ is F, $R^5$ is F, and $R^6$ is HC≡CH;

wherein where $R^1$ is H, $R^2$ is $OCH_3$, $R^3$ is H, $R^4$ is H, $R^5$ is H, and $R^6$ is HC≡CH; or wherein where $R^1$ is Cl, $R^2$ is Cl, $R^3$ is $CH_2OCH_3$, $R^4$ is Cl, $R^5$ is Cl, and $R^6$ is CH═C$(CH_3)_2$;

and optionally a carrier.

2. The composition according to claim 1, wherein said carrier is a volatile carrier.

3. The composition according to claim 1, wherein said carrier is camphor or a volatile essential oil.

* * * * *